United States Patent
Gettings et al.

(10) Patent No.: US 9,103,805 B2
(45) Date of Patent: Aug. 11, 2015

(54) ENVIRONMENTAL MEASUREMENT DISPLAY SYSTEM AND METHOD

(71) Applicant: Leeo, Inc., Palo Alto, CA (US)

(72) Inventors: Adam M. Gettings, Red Wing, MN (US); Eddy Y. Chan, Mountain View, CA (US); Andrew G. Stevens, Palo Alto, CA (US)

(73) Assignee: Leeo, Inc., Palo Alto, CA (US)

( * ) Notice: Subject to any disclaimer, the term of this patent is extended or adjusted under 35 U.S.C. 154(b) by 0 days.

(21) Appl. No.: 14/263,721

(22) Filed: Apr. 28, 2014

(65) Prior Publication Data

US 2014/0281479 A1  Sep. 18, 2014

Related U.S. Application Data

(63) Continuation of application No. PCT/US2014/029133, filed on Mar. 14, 2014.

(60) Provisional application No. 61/802,310, filed on Mar. 15, 2013, provisional application No. 61/847,079, filed on Jul. 16, 2013, provisional application No. 61/847,555, filed on Jul. 17, 2013, provisional application No. 61/858,563, filed on Jul. 25, 2013.

(51) Int. Cl.
| | |
|---|---|
| H04L 9/32 | (2006.01) |
| G01N 33/00 | (2006.01) |
| G06Q 30/02 | (2012.01) |
| G06Q 50/16 | (2012.01) |
| G06F 11/30 | (2006.01) |
| G06F 21/60 | (2013.01) |
| G06F 21/62 | (2013.01) |
| G06Q 10/08 | (2012.01) |
| G06Q 50/10 | (2012.01) |

(52) U.S. Cl.
CPC ........ *G01N 33/0062* (2013.01); *G06F 11/3089* (2013.01); *G06F 21/602* (2013.01); *G06F 21/6218* (2013.01); *G06Q 10/08* (2013.01); *G06Q 10/0832* (2013.01); *G06Q 30/0278* (2013.01); *G06Q 50/10* (2013.01); *G06Q 50/16* (2013.01)

(58) Field of Classification Search
None
See application file for complete search history.

(56) References Cited

U.S. PATENT DOCUMENTS

| | | | |
|---|---|---|---|
| 4,093,867 | A | 6/1978 | Shah et al. |
| 4,418,333 | A | 11/1983 | Schwarzbach et al. |
| 4,450,436 | A | 5/1984 | Massa |
| 4,896,039 | A | 1/1990 | Fraden |
| 5,045,833 | A | 9/1991 | Smith |

(Continued)

FOREIGN PATENT DOCUMENTS

GB  2454731  5/2009

OTHER PUBLICATIONS

Noh et al., "Design of a Room Monitoring System for Wireless Sensor Networks", Jul. 2013, pp. 1-7.

(Continued)

*Primary Examiner* — Brandon Hoffman
(74) *Attorney, Agent, or Firm* — Hudak Consulting Group LLC

(57) ABSTRACT

Environmental measurement display systems that can be used in home and commercial environments are disclosed. The environmental measurement display system can include an environmental sensor array, signal-processing circuitry, a power supply, a display device, a communications system, a data storage system, and a remote data visualization system.

21 Claims, 6 Drawing Sheets

(56) References Cited

U.S. PATENT DOCUMENTS

| | | |
|---|---|---|
| 5,156,203 A | 10/1992 | Funakoshi et al. |
| 5,159,315 A | 10/1992 | Schultz et al. |
| 5,646,591 A | 7/1997 | Issa et al. |
| 5,675,070 A | 10/1997 | Gelperin |
| 5,801,297 A | 9/1998 | Mifsud et al. |
| 6,023,223 A | 2/2000 | Baxter, Jr. |
| 6,428,334 B1 | 8/2002 | Skarie et al. |
| 6,492,907 B1 | 12/2002 | McCracken |
| 6,672,129 B1 | 1/2004 | Frederickson et al. |
| 6,753,776 B2 | 6/2004 | Drinkard |
| 6,753,786 B1 | 6/2004 | Apperson et al. |
| 7,089,780 B2 | 8/2006 | Sunshine et al. |
| 7,098,782 B1 | 8/2006 | Peckham et al. |
| 7,304,259 B2 | 12/2007 | Schwarz et al. |
| 7,337,078 B2 | 2/2008 | Bond et al. |
| 7,515,041 B2 | 4/2009 | Eisold et al. |
| 7,764,180 B2 | 7/2010 | Huang |
| 7,784,293 B2 | 8/2010 | Violand et al. |
| 7,818,184 B2 | 10/2010 | Penny et al. |
| 7,825,546 B2 | 11/2010 | Li et al. |
| 7,905,154 B2 | 3/2011 | Jones |
| 7,952,475 B2 | 5/2011 | Ivanov et al. |
| 7,994,928 B2 | 8/2011 | Richmond |
| 1,031,635 A1 | 12/2011 | Gruber et al. |
| 8,113,069 B2 | 2/2012 | Settles |
| 8,170,722 B1 | 5/2012 | Elberbaum |
| 8,242,640 B2 | 8/2012 | Lee et al. |
| 8,289,135 B2 | 10/2012 | Griffin |
| 8,301,271 B2 | 10/2012 | Lee et al. |
| 8,451,132 B1 | 5/2013 | Van Vleet |
| 8,475,367 B1 | 7/2013 | Yuen et al. |
| 8,489,437 B1 | 7/2013 | Dlott et al. |
| 8,605,091 B2 | 12/2013 | Bradbury et al. |
| 8,610,587 B2 | 12/2013 | Tropper |
| 8,639,391 B1 | 1/2014 | Alberth, Jr. et al. |
| 8,683,236 B2 | 3/2014 | Ukita et al. |
| 2002/0050932 A1 | 5/2002 | Rhoades et al. |
| 2002/0069076 A1 | 6/2002 | Faris et al. |
| 2002/0152037 A1 | 10/2002 | Sunshine et al. |
| 2003/0074092 A1 | 4/2003 | Carrabis |
| 2003/0227220 A1 | 12/2003 | Biskup et al. |
| 2004/0025604 A1 | 2/2004 | Call et al. |
| 2004/0069046 A1 | 4/2004 | Sunshine et al. |
| 2004/0075566 A1 | 4/2004 | Stepanik et al. |
| 2004/0147038 A1 | 7/2004 | Lewis et al. |
| 2004/0158193 A1 | 8/2004 | Bui et al. |
| 2005/0148890 A1 | 7/2005 | Hastings |
| 2005/0229452 A1 | 10/2005 | Shimasaki |
| 2006/0004492 A1 | 1/2006 | Terlson et al. |
| 2006/0173580 A1* | 8/2006 | Desrochers et al. .......... 700/276 |
| 2006/0250236 A1 | 11/2006 | Ackley et al. |
| 2006/0250260 A1 | 11/2006 | Albert et al. |
| 2007/0038334 A1 | 2/2007 | Chou et al. |
| 2007/0061393 A1* | 3/2007 | Moore .......................... 709/201 |
| 2007/0168088 A1 | 7/2007 | Ewing et al. |
| 2007/0225868 A1 | 9/2007 | Terlson et al. |
| 2007/0276548 A1 | 11/2007 | Uzunovic et al. |
| 2007/0278285 A1* | 12/2007 | Ehrensvaerd ................. 235/375 |
| 2008/0097809 A1 | 4/2008 | Stroman et al. |
| 2008/0106424 A1 | 5/2008 | Bouse |
| 2008/0173817 A1 | 7/2008 | Goldstein et al. |
| 2008/0211683 A1 | 9/2008 | Curt et al. |
| 2008/0221714 A1 | 9/2008 | Schoettle |
| 2008/0291036 A1 | 11/2008 | Richmond |
| 2009/0054799 A1 | 2/2009 | Vrtis et al. |
| 2009/0066513 A1 | 3/2009 | Kondo et al. |
| 2009/0096620 A1 | 4/2009 | Kuo |
| 2009/0141898 A1 | 6/2009 | Huang |
| 2009/0157839 A1 | 6/2009 | Diederichs et al. |
| 2009/0193578 A1 | 8/2009 | Jang et al. |
| 2009/0195382 A1 | 8/2009 | Hall |
| 2009/0271013 A1 | 10/2009 | Chen |
| 2010/0025449 A1 | 2/2010 | Longobardi |
| 2010/0090822 A1 | 4/2010 | Benson et al. |
| 2010/0101264 A1 | 4/2010 | Nishino |
| 2010/0145543 A1 | 6/2010 | Middlemiss |
| 2010/0235004 A1 | 9/2010 | Thind |
| 2010/0298957 A1 | 11/2010 | Sanchez Rocha et al. |
| 2010/0306033 A1 | 12/2010 | Oved et al. |
| 2010/0318236 A1 | 12/2010 | Kilborn et al. |
| 2011/0025499 A1 | 2/2011 | Hoy et al. |
| 2011/0108724 A1 | 5/2011 | Ewing et al. |
| 2011/0187542 A1 | 8/2011 | Dittmer et al. |
| 2011/0202193 A1 | 8/2011 | Craig et al. |
| 2011/0216453 A1 | 9/2011 | Haines et al. |
| 2011/0245988 A1 | 10/2011 | Ingels et al. |
| 2011/0260851 A1 | 10/2011 | Richman |
| 2011/0270458 A1 | 11/2011 | Liu |
| 2011/0273283 A1 | 11/2011 | Schmuttor et al. |
| 2012/0022886 A1 | 1/2012 | Ohnemus |
| 2012/0023555 A1 | 1/2012 | Putterman |
| 2012/0095610 A1 | 4/2012 | Chapel et al. |
| 2012/0109398 A1 | 5/2012 | Bhakta |
| 2012/0154126 A1 | 6/2012 | Cohn et al. |
| 2012/0209634 A1 | 8/2012 | Ling et al. |
| 2012/0265361 A1 | 10/2012 | Billingsley et al. |
| 2012/0303554 A1 | 11/2012 | Osann |
| 2012/0316661 A1 | 12/2012 | Rahman et al. |
| 2012/0325023 A1 | 12/2012 | Calio et al. |
| 2013/0082817 A1 | 4/2013 | Gruenbacher et al. |
| 2013/0085609 A1 | 4/2013 | Barker |
| 2013/0166089 A1 | 6/2013 | Craig et al. |
| 2013/0174646 A1 | 7/2013 | Martin |
| 2013/0184880 A1 | 7/2013 | McMahon |
| 2013/0201033 A1 | 8/2013 | Cohn at al |
| 2013/0238153 A1 | 9/2013 | Warwick et al. |
| 2013/0275148 A1 | 10/2013 | Attaluri et al. |
| 2014/0006506 A1 | 1/2014 | Frei et al. |
| 2014/0025221 A1 | 1/2014 | Chapel et al. |
| 2014/0032003 A1 | 1/2014 | Chapel et al. |
| 2014/0069131 A1 | 3/2014 | Masui |
| 2014/0098445 A1 | 4/2014 | Hooper |
| 2014/0100700 A1 | 4/2014 | Matsumoto et al. |
| 2014/0156084 A1 | 6/2014 | Rahman et al. |
| 2014/0188286 A1 | 7/2014 | Hunka |
| 2014/0236372 A1 | 8/2014 | Ewing et al. |
| 2014/0257572 A1 | 9/2014 | Mohan et al. |

OTHER PUBLICATIONS

Carriazo-Osorio, Fernando, "Impacts of Air Pollution on Property Values: an Economic Valuation for Bogota, Colombia", http://www.demogr.mpg.de/papers/workshops/01_0518yaper02.pdf, Aug. 19, 2007.

Hayashi et al., "A Network-Centric Approach to Sensor-data and Service Integration," Sep. 13-18, 2011, SICE Annual Conference, pp. 2037-2042.

Huang et al., "Pervasive, Secure Access to a Hierarchical Sensor-Based Healthcare Monitoring Architecture in Wireless Heterogeneous Networks," May 4, 2009, IEEE Journal on Selected Areas in Communications, vol. 27, No. 4, pp. 400-411.

Miyaho et al., "Sensor Network Management for Healthcare Applications," 2010, IEEE Computer Society, pp. 14-20.

* cited by examiner

ENVIRONMENTAL MEASUREMENT DISPLAY SYSTEM AND METHOD

CROSS-REFERENCE TO RELATED APPLICATION

The present application is a continuation of PCT Application No. PCT/US2014/029133, filed 14 Mar. 2014, which claims priority to U.S. Provisional App. No. 61/802,310, filed 15 Mar. 2013; U.S. Provisional App. No. 61/847,079, filed 16 Jul. 2013; U.S. Provisional App. No. 61/847,555, filed 17 Jul. 2013; and U.S. Provisional App. No. 61/858,563, filed 25 Jul. 2013, all of which are incorporated by reference herein in their entireties.

TECHNICAL FIELD

Environmental measurement display systems and methods are disclosed relating generally to the field of air quality measurement.

BACKGROUND

Humans are capable of detecting both toxic and non-toxic chemicals with their sense of smell and without specialized training it can be difficult for humans to differentiate between safe chemicals and harmful chemicals. Some chemicals can be harmful in concentration, but harmless in small amounts, and it can be difficult for humans to differentiate between safe and harmful levels by smell alone. Finally, the definition of safe and harmful levels can vary depend on the environment and on individual sensitivity of a person (or a product stored in an environment). Thus, there is a need in the environmental sensor field to create a new environmental measurement display system and method.

Real estate derives a great deal of value from environmental quality of both air and water. A verifiable environmental report for a property showing excellent, neutral or poor environmental quality can have a direct effect on the price of both residential and commercial real estate, as well as rental, leasing and hospitality rates. It would be to the advantage of a real estate owner or seller to demonstrate the quality of their environment, and a financial premium estimate for a good environmental score, and a financial penalty estimate for a low environmental score can be assigned, allowing buyers and sellers to properly value property in many different transactions and environments.

Perishable goods can go bad if not stored properly, and things like grains, eggs, meat, fish, seafood, dairy products, and produce can be sensitive and cause food poisoning if not stored properly. Perishable products verifiably stored in proper environments may be sold at a premium to other products not necessarily verifiably stored in proper environmental conditions. For example, Kobe Beef stored in optimal conditions can be certified as premium stored, and can be sold for a higher premium, depending on the quality of the environment. Similar to how diamonds are graded, even though the naked eye cannot tell the difference, a finer measurement can differentiate between quality, and this measurement for perishable goods can be the storage environment.

Valuable documents or antiques require specific environments to ensure they maintain their condition and value. An antique that has been stored in an optimal environment can be expected to sell for a premium, and an environmental sensor measurement of the storage environment can verify the quality of the storage environment.

Accordingly, a system and method for tracking and reporting the environmental quality and the respective impact on the value for specific real estate, perishable goods, and valuable documents or antiques is desired.

SUMMARY OF THE INVENTION

A system for monitoring air quality in an environment is disclosed. The system can have a first air quality sensor array located in the environment, a microprocessor connected to the sensor array, a power source having a wall plug, a server, and a first wireless communication system. The wireless communication system can be connected to the microprocessor. The communication system can be configured to transmit data from the first sensor array to the server.

A method for monitoring air quality in an environment is disclosed. The method can include plugging an air quality monitoring system into a wall power outlet in the environment. The air quality monitoring system can have a first air quality sensor array. The method can include sensing an air quality factor in the environment with the first air quality sensor array. The method can include converting the air quality factor into a data signal, where the converting can be performed by the air quality monitoring system. The method can include wirelessly transmitting the data signal from the air quality monitoring system to a server.

Furthermore, a method for monitoring air quality in a first environment and a second environment is disclosed. The method can include positioning a first air quality monitoring system in the first environment. The first air quality monitoring system can have a first air quality sensor array. The method can include positioning a second air quality monitoring system in the second environment. The second air quality monitoring system can have a second air quality sensor array. The method can include sensing an air quality factor in the first environment with the first air quality sensor array, and sensing the air quality factor in the second environment with the second air quality sensor array. The method can include converting the first air quality factor into a first data signal with the first air quality monitoring system, and converting the second air quality factor into a second data signal with the second air quality monitoring system. The method can include wirelessly transmitting the first and second data signals to a server.

Also disclosed is an environmental monitoring system that can have a first sensor system, a server and a data storage device. The first sensor system can be located in a first environment. The first sensor system can be configured to measure a first environment quality factor and output first sensor data. The server can be configured to receive the first sensor data from the first sensor system. The server can be configured to process the first sensor data and output first economic data for the first environment. The data storage device can be configured to store the first economic data for the first environment.

An environmental monitoring method is disclosed that can include detecting a first environmental quality factor in a first environment with a first sensor system. The method can include outputting a first sensor system data from the first sensor system. The method can include receiving the first sensor system data by a server. The method can include calculating by the server a first economic data for the first environment. The server can use the first sensor system data in the calculation.

A further environmental monitoring method is disclosed. The method can include detecting at a first time with a first sensor system a first environmental quality factor in a first environment. The method can include outputting a first sensor system data from the first sensor system. The method can include the server receiving the first sensor system data. The method can include the server comparing a first economic data for the first environment to a second economic data. The comparing by the server can include outputting an economic delta for the first environment. The economic delta can be a difference in the economic state, for example over time or in comparison to another environment or environmental factor.

A property monitoring system for monitoring property at a first location is disclosed. The system can have an environmental sensor system at the first location. The environmental sensor system can be configured to produce data on an environmental quality factor. The system can have a first data storage system configured to have a first database in communication with the environmental sensor system, wherein the first database is configured to have data on a market value for the property. The system can have a processor configured to calculate a product value by modifying the market value with the data for the environmental quality factor.

Additionally disclosed is a method for monitoring property at a first location. The method can include sensing an environmental quality factor at the first location. The sensing can be performed with an environmental sensor system. The method can include retrieving a market value for the property from a first data storage system. The method can include calculating with a processor a product value for the property by modifying the market value with the data for the environmental quality factor.

Furthermore, a method for monitoring property at a first location is disclosed. The method can include attaching an environmental sensor system to the property. The method can include sensing an environmental quality factor at the property. The sensing can be performed with the environmental sensor system. The method can include retrieving from a first data storage system a market value for the property. The method can include calculating with a processor a product value of the product by modifying the market value with the data for the environmental quality factor when the sensor system is attached to the property.

An environmental monitoring method is disclosed. The method can include sensing an environmental quality in a first environment. The sensing can be performed with an environmental quality monitoring system. The sensing can produce environmental data.

The method can include recording the environmental data in a first database. The method can include encrypting the environmental data. The method can include transmitting the environmental data from the first database to a first computer, such as a computer executing a web browser and searching for the environmental data. The method can include decrypting the environmental data on the second computer.

Disclosed is an environmental monitoring method that can include sensing environmental quality data in a first environment. The method can include attaching location data to the environmental quality data to form composite data. The method can include recording the composite data in a first database, and transmitting the composite data from the first database to a computer.

An environmental monitoring method is disclosed that can include sensing environmental quality data in a first environment, and attaching a timestamp to the environmental quality data to form composite data.

A method of displaying environmental quality measurements is disclosed. The method can include measuring the output of a first environmental sensor, recording the output of a first environmental sensor, generating a report from the output of at least one environmental sensor, and assigning a commercial value to a location monitored by at least one environmental sensor. The commercial value can be assigned to an environment in real time. The method can communicate the commercial value to a user, as well as a personalized value in real time that relates to an individual's requirements at any given time due to their health condition and other personalized factors. The user could be a pet, for example a cat and dog or different breeds may need or thrive in different air quality environments.

The method can include sharing or reporting any of the recorded, generated or assigned information. Recording the output of at least one environmental sensor can include encrypting the recorded output of the at least one environmental sensor. The recorded output can be encrypted with an encryption key associated with a user. The sharing or reporting the information can include decrypting the recorded output of at least one environmental sensor using an encryption key associated with a user.

Assigning a commercial value to a location monitored by at least one environmental sensor further can include computing a commercial value using a function derived from a plot of pricing data and environmental quality data.

A method of displaying environmental quality measurements is disclosed. The method can include measuring the output of at least one environmental sensor, recording the output of at least one environmental sensor, generating a report from the output of at least one environmental sensor, and assigning a commercial value to a product stored at a location monitored by at least one environmental sensor.

The assigning of the commercial value to the product stored at the location monitored by the at least one environmental sensor can include computing a commercial value using a function derived from a plot of product pricing data and environmental quality data.

The data processor of the system can display or send a maintenance notification when a sensor data value crosses a threshold. For example, if the sensor crosses an air particulate threshold, the system can display or send a notification (e.g., to the server or a computer or smartphone connected by Bluetooth or Wifi) to change an air filter in the environment's HVAC system. If the sensor crosses an time threshold, the system can display or send a notification to perform a scheduled maintenance task (e.g., clean the system or the environment). If the sensor crosses an animal dander count threshold, the system can display or send that the animals in the environment need to be washed. If the sensor crosses a calibration threshold, the system can display or send that the sensor needs to be replaced. If the sensor crosses a power threshold, the system can display or send that a battery in the system needs to be replaced. If the sensor crosses a toxic chemical threshold, the system can display or send that a danger exists.

DETAILED DESCRIPTION

Figure 1:
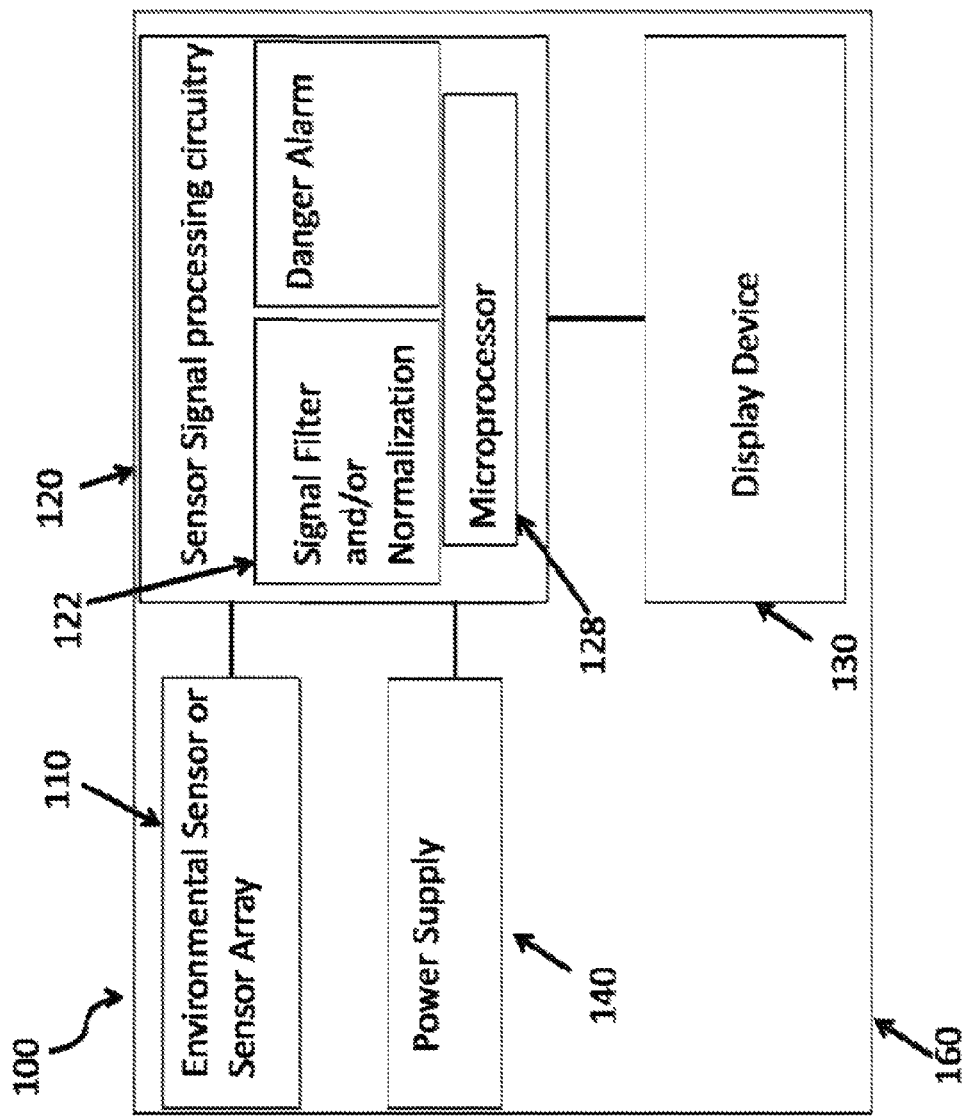
FIG. 1 is a diagram of a variation of an environmental measurement display system.

FIG. 1 illustrates a variation of an environmental measurement display system 100. The system can be used in a home, commercial environment (e.g., office, industrial environment, hospitality environment, warehouse, shipping container, airplane cabin, ship cabin, train car, liquid storage tank (for transporting food grade products, medical grade products, fuel products, water, or any other liquid), disposable packaging such as a produce container or a lobster box, or combinations thereof), to monitor the quality of their environment. Environmental quality factors can include air quality factors, such as levels of organic compounds or allergens. The system 100 can display that the quality of the environment is good and stable or that there is a potentially harmful or allergenic environment that may need to be addressed.

The environmental measurement display system 100 can include an environmental sensor array 110, signal-processing circuitry 120, a power supply 140, and a display device 130.

Figure 2:
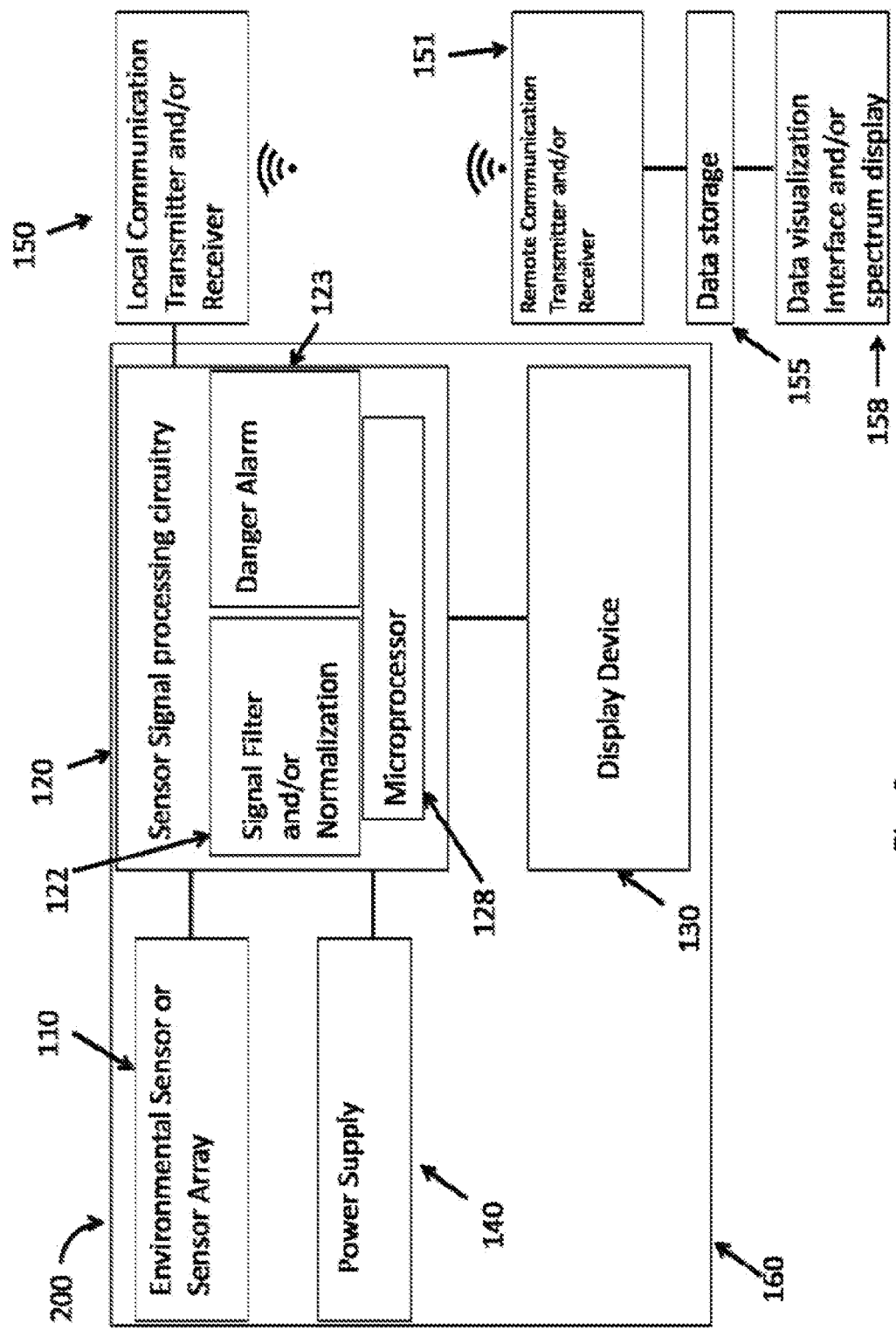
FIG. 2 is a diagram of a variation of the environmental measurement display system.
Figure 3:
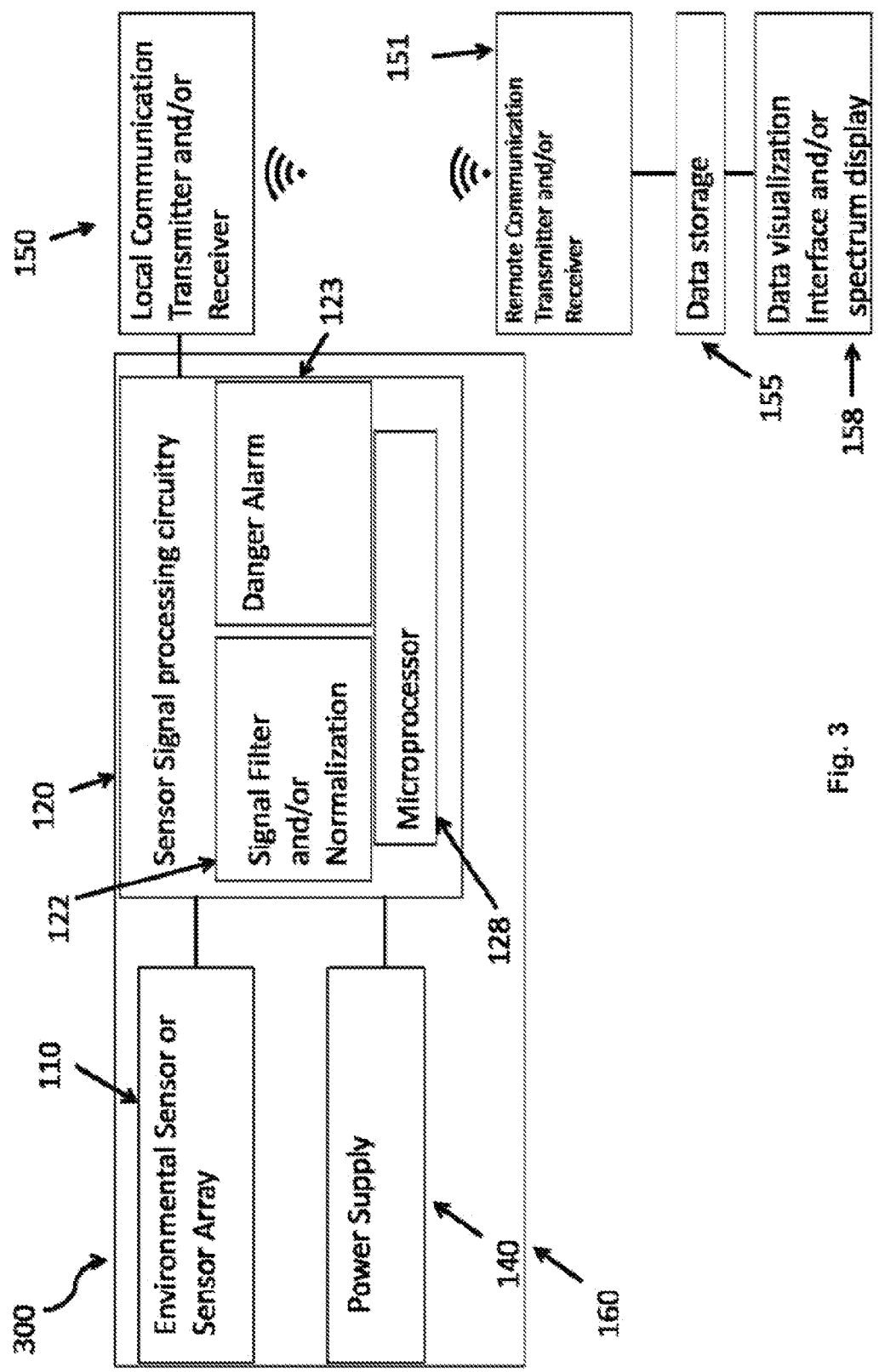
FIG. 3 is a diagram of a variation of the environmental measurement display system.

FIG. 2 illustrates that the display systems 200 can have visual interfaces and external devices for collecting and visualizing environmental data. FIG. 3 illustrates that the environmental measurement display system 300 can have no local display device 130.

FIGS. 2 and 3 illustrate that the environmental measurement display systems 200 and 300 can include a communications system 150, a data storage system 155, a remote data visualization system 158 and a chassis 160.

The environmental sensor array 110 can measure properties of an environment in which the environmental measurement display system 100 is located. The environmental sensor array 110 can have one or more sensors such as mass spectrometers, nano-plasmonic sensors, chemical sensors, optical particle sensors, ionization particle sensors, barometers, thermometers, humidity sensors, oxygen sensors, carbon dioxide sensors, nitrogen sensors, smoke detectors, accelerometers, GPS's, Geiger counters, CMOS/CCD image sensors. RF radiation detectors, or combinations thereof. The array 110 can have one or more sensors of each type, for example for redundancy in the event of a sensor failure or erroneous reading, and/or for improved accuracy and/or precision. The sensor array 110 can include at least one particle sensor for detecting allergens such as dander, pollen, dust, exhaust, carbon monoxide, radon and smoke. The sensor array 110 can include sensors for detecting exposure time and/or concentration levels of volatile organic compounds, particle size, particle counts in air and/or in water.

The signal processing circuitry 120 can remove noise from signals received from sensors in the environmental sensor array 110. The signal processing circuitry 120 can normalize at least one signal from the environmental sensor array 110 and can convert at least one signal from the environmental sensor array 110 to a suitable output for a display 130. For example, the environmental sensor array 110 can generate a chemical level signal corresponding to a chemical level present in the air. The signal processing circuitry 120 can convert the chemical level signal to a signal that can be processed by a display device 130.

The signal processing circuitry 120 can include signal filters 122, a mixed signal processing integrated circuit, a mixed signal microprocessor 128, such as those made by Texas Instruments, or combinations thereof. The signal processing circuitry 120 can include encryption hardware or software to encrypt the signal data.

The conditioning or signal processing circuitry 120 can include a danger alarm 123. The danger alarm 123 can be a lower level circuit that can sound an alarm when a harmful level of at least one chemical is detected, for example if an attached display device 130 is malfunctioning, disconnected, broken or otherwise disabled. The danger alarm 123 can sound an alarm with a speaker or other audio transducer, such as a smoke detector alarm sound mechanism. The danger alarm 123 can use a network connection of a communications device to transmit an alarm to a central communications station where a user or person in the environment can be contacted, notified and can either investigate the problem, or evacuate the area and wait for a chemical response team.

The sensor array 110 can detect air particles, such as dust, dander and other allergens, and can send a notification via the processor or danger alarm 123 to a server, other system, computer, or handheld device connected by wired or wireless (e.g., Bluetooth, Wifi) communication to the system 100 in the environment with instructions to perform an environmental clearing action such as ventilating the area, changing an air filter, turning on a filtration system, running a humidifier, or combinations thereof. When a human activity or a machine-controlled activity is causing changes to the environment, the danger alarm 123 can encourage the changes (if they are positive, such as ventilation), or discourage the changes (if the environmental changes are negative) by sounding an alarm or sending a notification to a user or a machine. The danger alarm 123 can suggest safety tips and precautions such as advising a human to wear a mask while vacuuming an environment with dangerous levels of dust, or advising a human or a machine to ventilate an area, and/or slow down the rate of application of a chemical product or paint and/or use personal protection equipment such as a ventilation mask. When the system 100 detects that food is being burned in a kitchen, the danger alarm 123 can notify a human immediately, instead of waiting for the human nose to detect the burning smell.

Multiple danger alarms 123 can be used simultaneously, and can have different notification sounds, lights, notification methods or messages. For example, a smoke detection sound could be different from a sound played when a dangerous level of dust is detected.

The display device 130 can display signal information from the sensor array 110 and/or processed signals from the signal processing circuitry 120. The environmental monitoring system 100 can operate (e.g. take measurements and/or notify users of dangerous levels) when the display device 130 is broken or non-functioning. The display 130 can be calibrated to display a range of values and information, including numerical measurements, or just simply shades of grey or colors on a spectrum. The display device 130 can be an organic light emitting diode (OLED) display, a color liquid crystal display (LCD), a binary LCD, a gray scale LCD, a grayscale e-ink display, a color e-ink display, a Braille output device, laser projection display, or combinations thereof. The display device 130 can be a remote display device, for example a monitor on a computer which can be displaying an Internet browser, a smartphone or a tablet screen displaying a remote smartphone application, a monitor or screen displaying the output of a computer program executing on a hardware chip, or combinations thereof.

For example, as a harmful chemical is detected by a sensor array 110, and processed by signal conditioning or processing circuitry 120, the display device 130 can display the processed signal in a user-comprehendible format. The user-comprehendible format can be a color, numbers, chemical formulas, images, chemical images, structural chemical formulas, tessellations with gradients of larger or smaller element sizes, tessellations of increasing or decreasing element sizes (e.g. as a larger or smaller magnitude of signal is detected, the element size in the tessellation is adjusted to be larger or smaller) or combinations thereof.

The display device 130 can display textures, patterns or colors can be displayed on binary LCD, grayscale LCD, grayscale c-ink display, color LCD, or color-e-ink display, or any other display capable of displaying patterns. The parameters such as textures, patterns, images or colors can correspond to detected chemical levels. For example, the display device 130 can display a hex texture or pattern when benzene is detected. As the system 100 detects increasing levels of benzene, the display device 130 can change the size, scale, darkness, pitch, color, dimension, perspective (converting from 2-D to 3-D), visualization orientation, or combinations thereof of the hex pattern. The display device 130 can change color (either the background color or the foreground color) of one or more displayed images in response to changes in the chemical signals detected by the system 100. For example, as the system 100 detects increasing level of benzene on an absolute scale, the display device 130 can change the displayed colors from a light green to a yellow to orange to red (with red indicating a harmful level of benzene present in the air). The colors could increase or decrease tint, saturation, hue, contrast, brightness, transparency, fade, or combinations thereof.

The display device 130 can show graphics that can include a pie chart, a bar chart, a scatter plot, a time-series plot, or any other suitable graphical analysis, to provide a user with information about the chemicals in the environment. The display device 130 can show images of chemicals, color scales or numbers. The display device 130 can grow or shrink the displayed image of the chemical proportionally relative to the chemical levels detected by the system 100 (e.g., scaling up or down). The display device 130 can show graphics that can include sensor life, system uptime, system maintenance data or commands and recommendations (e.g. change a sensor, clean a sensor, calibrate a sensor), battery life remaining, wireless or wired signal connectivity, danger alarms enabled or disabled, status messages, or combinations thereof.

Figure 4A:
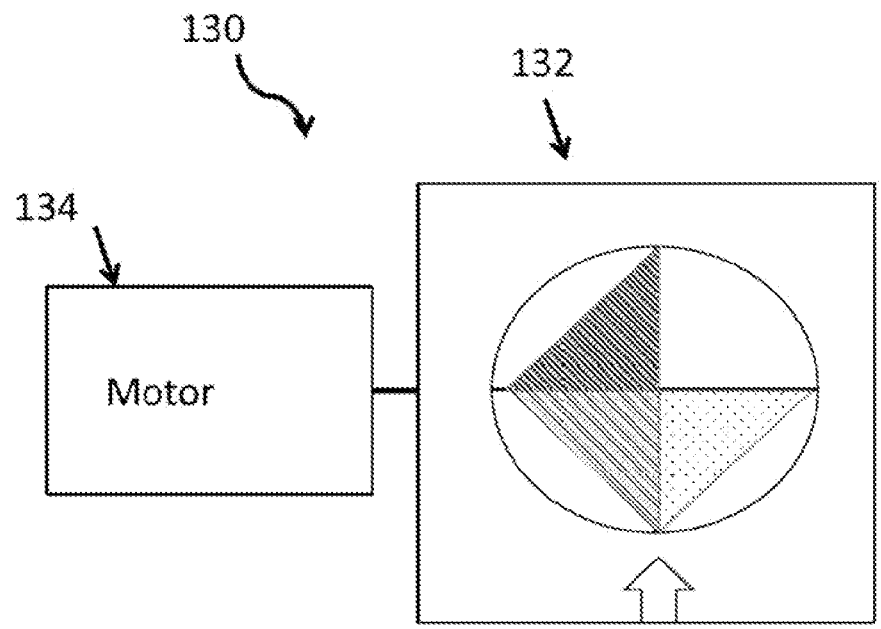
FIGS. 4A and 4B are diagrams of variations of a display device of the environmental measurement display system.
Figure 4B:
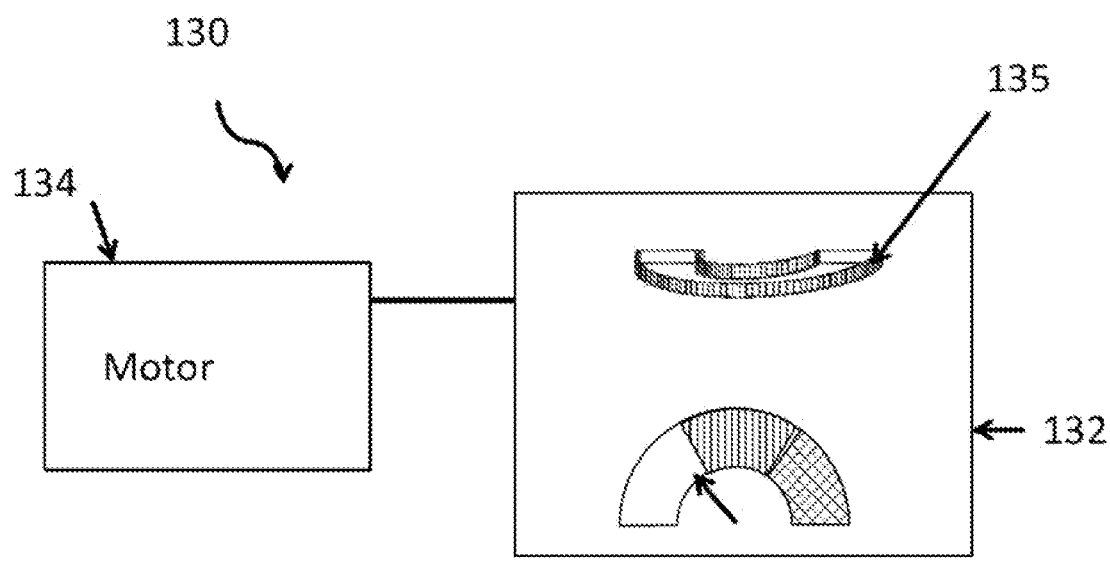

FIGS. 4A and 4B illustrate that a display device 130 can include at least one color wheel display 132 and at least one motor 134. The color wheel indicator 132 can include an arrow or other marker that can be aligned with the color wheel to indicate which area on the color wheel corresponds with the current environmental quality measurement level.

FIG. 4b illustrates that the upper half of the color wheel indicator 132 can have a rotatable ring 135. The rotatable ring 135 can have a band of color along the outside or shades of grayscale on the outside of the ring 135, such that a user can identify the approximate level of environmental quality from the colors displayed on the ring 135.

The lower half of the color wheel indicator 132 can include a color or texture based gauge. Multiple color wheel indicators 132 can be used together to display additional information, for example to provide additional resolution and/or precision to the display. For example, a transparent color wheel with additional colors could be rotated by an additional motor or the same motor 134 (possibly rotated at a different rate using gearing) to modify the colors presented. An additional color wheel can be shades of grey. An additional color wheel can be a transparency filter. At least one color wheel can include transparent gradients around the ring or the color wheel of increasing opacity of Red, Green, and Blue, and/or Cyan, Magenta, Yellow.

The motor 134 in the display device can move or rotate the color wheel or a color ring in a color wheel indicator 132. The motor 134 can receive signals from the signal conditioning or processing circuitry 120 and can actuate the color wheel indicator 132 to display a color on the color wheel that corresponds to the signal that has been measured by the sensor array 110, and then processed by the signal conditioning circuitry 120. Using the motor 134 to control the color wheel indicator 132 can use less power than an active, or even passive display device, such as an LCD, or an e-ink screen. The motor 134 can be a small DC brushed motor, a brushless DC motor, a piezo type ratcheting motor, or combinations thereof. The motor 134 can be controlled using a control loop to track position and can use homing sensors (either optical sensors, magnetic sensors, or any other suitable sensor) as a control scheme for the motor 134. The motor 134 can home to a zero-position, and then run open-loop. The motor 134 could run in a closed-control loop using an encoder, such as an optical encoder, a mechanical encoder, a potentiometer, or combinations thereof.

The power supply 140 can power the electronics for the other elements of the system, including a sensor array 110, signal conditioning circuitry 120, display device 130, communications system 150, and other components in the system that require power. The power supply 140 can be a transformer for an alternating current, such as standard wall socket plug or a direct wiring to a home or building electric grid, a mechanical generator, a diesel generator, or any combinations thereof. The power supply 140 can also be a battery, a DC current power supply, a DC current from a computer (for example through a USB port), a photodiode, a photovoltaic cell, or combinations thereof.

The chassis 160 can physically fix to, support, and/or orient the components of the system 100. The chassis 160 can support the orientation of the sensor array 110, and a grating in the chassis could prevent large particles, soil and mud from damaging or otherwise obscuring inputs into the sensor array 110. The chassis 160 can support at least one display 130 and can either house a power supply 140, such as a battery, a power supply plug, a photodiode, a photovoltaic cell, a power plug, a collapsible power plug, a power plug and transformer combination.

The local communication device 150 can communicate with a remote device, and can transmit signal data generated by a sensor array 110 and conditioning circuitry 120 to a remote device for monitoring, storage, notifications, or combinations thereof. The communication device 150 can be a wireless or a wired device. The wireless device can be a WiFi device, a mobile data modem (such as a 2G, 3G, 4G LTE device), a Zigbee communication device, a Bluetooth device, a wireless USB device, infra-red transmitter, an ethernet over electrical grid connection, or combinations thereof.

FIGS. 2 and 3 illustrate that the remote communication device 151 can receive data from the local communication device 150, and store the received data on a data storage device 155. The data can be control signal data, environmental data generated from a sensor array 110 and signal conditioning circuitry 120, alarm data generated by a danger alarm 123, battery power charge remaining, or any combinations thereof.

The remote communication device 151 can be directly connected to the local communication device 150. The devices 150 and 151 can be connected on the same board or the same chip, connected by an Ethernet cable, connected by a wireless channel, or combinations thereof. The remote communication device 151 can be directly connected to a data storage device 155. The remote communication device 151 can be connected to a data storage device 155 through an internet connection (e.g., wired, wireless WiFi, 3G, 4G, LTE, or any other suitable wireless connection), acting as a hub. A single remote communication device can function as a hub for at least one sensor device and/or connect and transmit data to and from multiple sensor systems 100 and at least one data storage device 155.

The data storage device 155 can store the signals produced by the sensor array. The stored signals can be post processed, time-stamped for time series processing, filtered, compressed, or analyzed before storing. The data storage device 155 can be a storage system such as a networked computer server, including a database on a hard disk, a database stored in volatile or non-volatile memory, data stored in a text file, data stored on multiple servers comprising a distributed database server platform, or combinations thereof.

The data visualization interface 158 can visualize the stored data. The data visualization interface 158 can display information such as reports, charts, time series plots, pie charts, spectrums, spectrograms, or combinations thereof. The data visualization interface 158 can generate a report as an image file and/or a document (such as a Microsoft word document or a PDF document) and send the visualization via email or MMS message to a user. The data visualization interface 158 can be a website accessible via a web browser where a user can select at least one type of report generated from the signal data generated by their sensor device.

The data visualization interface can provide anonymized comparisons with neighbors or similar classes of users, to enable a user to compare the environment where the sensor has been placed with comparable locations, and providing a relative comparison for health, safety, and/or general interest. The data visualization interface 158 can operate as a smartphone (i.e., mobile) application, such that the phone can provide the display and a user interface for the data visualization, for example, allowing the selection of a type of time series chart, and enabling a user to zoom in on the chart graphic by sliding their fingers apart on the screen.

A mobile application can enable remote monitoring of the system 100 by the remote communication device 151 from a remote or local location. For example, users can monitor environmental data of remote storage sites, homes, or offices. A data visualization interface 158 can include a selection mechanism to determine a display type (e.g. a selection box or a slider bar with options such as basic, intermediate or advanced—depending on the technical level of the user, or the application purpose of the environmental sensor device). Configuration of a danger alarm 123 notifications and alerts, danger alarm threshold levels and other settings can be configured from the data visualization interface 158. The data visualization interface 158 can allow a user to decrypt the information from an environmental sensor device. For example an encryption key could be stored on the outside of the device, and a user can enter the encryption key to decrypt the information prior to sharing, and/or generating a report.

The remote communication device 151 can be a smartphone, a tablet, or a computer, an embedded system appliance (e.g. a hub) or other suitable device. The remote communication device 151, the data storage device 155 and the data visualization interface 158 could be located on a remote webserver, a user's smartphone, a home computer, a regional computer of a landlord or property manager or organization. A Zigbee dongle can be configured to be the remote communication device 151 for a specific environment (e.g., a home or office), and can then function as a data storage device 155 and a data visualization interface 158, and perform any processing and or communication with a remote data server (e.g. reporting for corporate compliance or offsite data storage). Similarly, a smartphone can have a Zigbee attachment or built in Zigbee connectivity, or use Bluetooth to as the remote communication device 151, and use the memory on the phone as storage device 155, and the user interface on the phone as the data visualization interface 158.

A second chassis can include a remote communication device 151, and can store the received sensor data on a local data storage device 155, and/or transmit the data further to a remote computer server system over the internet or a network, for storage on a remote data storage device 155, and subsequent visualization on a data visualization device 158. The second chassis can include a second sensor array in the second chassis. The second sensor array can confirm and/or calibrate sensor readings from the first environmental sensor array 110 in the environmental measurement display system 100, and can improve power consumption and sensor sensitivity. If the environmental sensor array 110 receives potentially erroneous readings or data (e.g., the data is outside of 0% to 100% of a historical range or outside of a 5% to 95% historical range for the array 110), the data from the first and second sensors arrays can be compared before sounding an alarm locally with a danger alarm 123, or communicating to a cloud based data visualization interface 158.

The data visualization interface 158 can generate reports such as maintenance reminders for an environment (such as changing an air filter, opening a window for ventilation, taking out the garbage), notifications of dangerous levels of chemicals, reports for various time periods (e.g. weekly, or monthly trends in their local environment), an environmental quality rating over time, a value premium estimate for a residential or commercial property based upon the environmental quality observed over time, an insurance premium computation, a cost-of-damage assessment, or combinations thereof. The data visualization interface 158 can process data using data from numerous users to determine optimized thresholds and danger alarm levels.

The system 100 (e.g., the microprocessor 128) can execute artificial intelligence algorithms to determine optimal settings for a particular device, environment, building type, user application, and/or user class, and the results can be transmitted to the particular device to improve performance (e.g. calibration, power consumption, safety, accuracy, precision of devices of the environmental sensor display system). The settings for a particular device can be calibrated for an individual building, or the settings can be tested on a similar device in similar conditions and provide a generic "building type" calibration.

Methods of Use

The environmental sensor system 100 can be in communication with non-environmental sensor systems, such as home automation consoles, automobile control consoles, smartphones, tablets, computers and combinations thereof. The system 100 can display environmental quality measurements with the non-environmental sensor systems.

Figure 5:
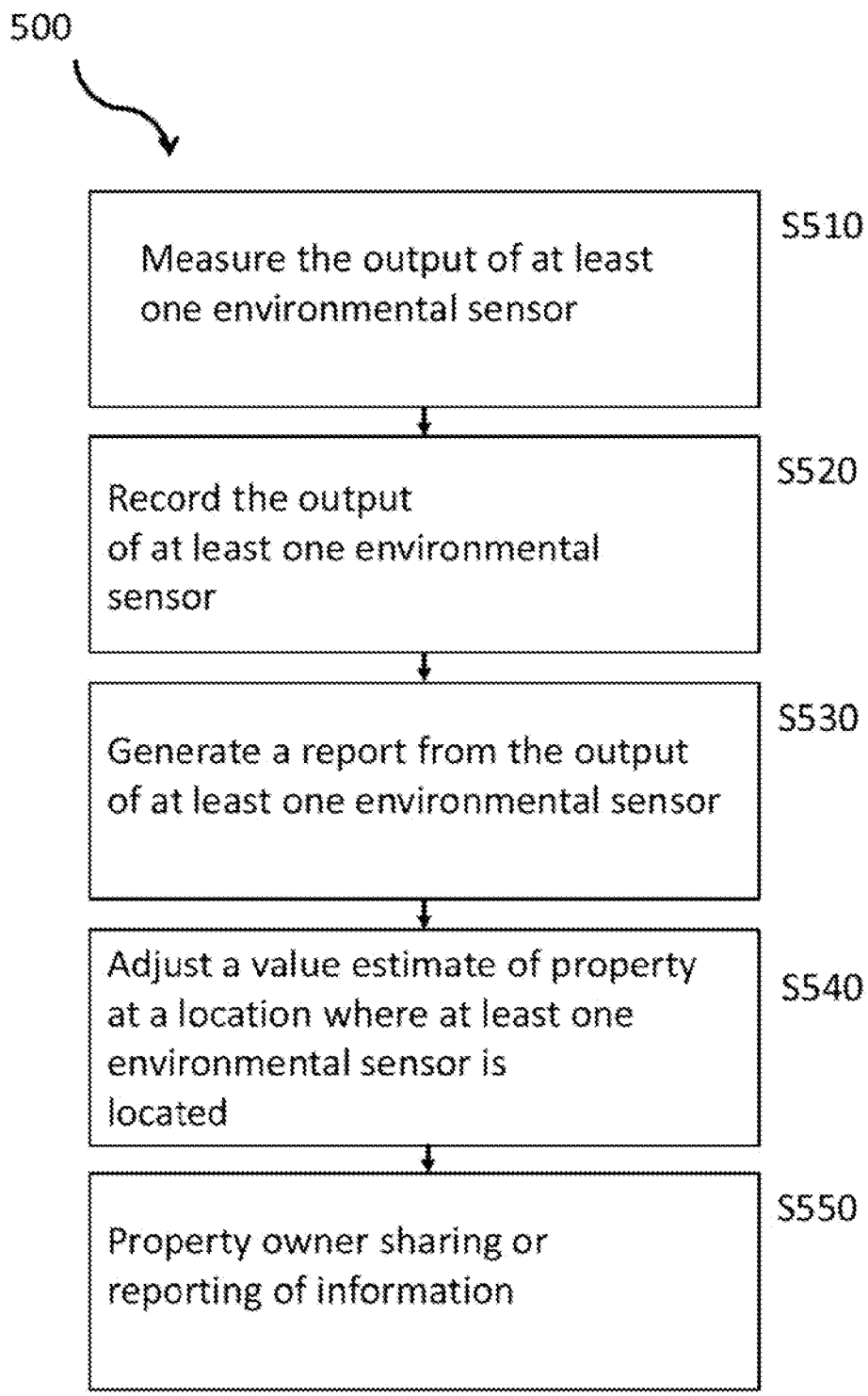
FIG. 5 is a flowchart of a method of displaying environmental quality measurements.

FIG. 5 illustrates that a method 500 of displaying environmental quality measurements can include measuring the output of at least one environmental sensor S510, recording the output of at least one environmental sensor S520, generating a report from the output of at least one environmental sensor S530, adjusting the value estimate of property at a location where at least one environmental sensor is located S540, and property owner sharing or reporting of information S550.

The measuring S510 can include signal conditioning to remove noise, comparing multiple signals from multiple sensors of the same type, and/or encrypting the signal.

The recording S520 can include recording signal data from at least one environmental sensor measurement. The recording S520 can include processing such as filtering, timestamping (e.g., recording time data when the data was collected, sensed, recorded, and/or received), encrypting or combinations thereof. The recording S520 can include storing the signal data in a computer database in a device that can receive, store and process data such as on a server, distributed across many servers, a home or office computer, a tablet, a smartphone, or combinations thereof.

The report generating S530 can include the system 100 generating the reports from environmental sensor data. The system 100 can process at least two points of the recorded environmental sensor data in a time series to generate a time series plot of environmental quality.

Before or after generating the report, the system 100 can receive a decryption key (e.g., entered by a user) to decrypt the stored data from the user-owned sensor device. The system 100 can use the decryption key to decrypt the data. A data storage device can be maintained or operated by a third party (e.g., not part of the system) and servers managing the data storage device may not have access to the decryption key.

For example, the data can be encrypted before the data is stored, and the decryption key can be physically displayed on the system 100 (for example attached to an environmental sensor system 100 on a sticker). The system operator can be the only person to have access to data generated by their own device, and would have to authorize the sharing of that information. Smartphone applications or data visualization interfaces, or internet browser based web applications could require a decryption key before accessing the data, further protecting a user's information from third parties that may have an interest in obtaining the data. If accelerometer and/or GPS sensor data is collected, a report can be validated or invalidated based upon detected movement of a sensor.

Estimated property values can be stored in a computer memory in the system 100 or in a remote database, for example, not part of the system 100. The system 100 can adjust S540 or assign the estimated property value at a location where at least one environmental sensor is located. The property value can be a commercial value of real estate, antiques, and/or perishable goods which derive value from the quality of their respective environments. The adjustments or assignments of the property value by the system 100 or a separate computer can be calculated from one or more scaling or weighting factors (e.g., time decay scaling based on the time since the data was recorded, location scaling based on the location of the sensor array, factor scaling such as a first weighting for a first allergen or toxic chemical and a second weighting for a second allergen or toxic chemical, environment scaling based on which environment the sensor array is located) read by the system 100 from a database, the type of property (e.g., house, office, strawberries in a storage container, antique painting), and the current and/or historical environmental data recorded by the system 100.

The system 100 can share S550 the generated reports and/or value adjustments or assignments with other computers over a network (e.g., over the Internet). The system 100 can attach verification or certification data to the reports and/or value adjustments.

For example, property owners can share or report information or reports on the environmental quality of their property (if they so desire, but also possibly compulsory, if regulations require compulsory reporting). For example a butcher could report on the quality of the environment in their meat locker, and be able to demonstrate the superior quality of their meats. A homeowner could report the excellent air quality in their basement to prospective buyers, as a commercial landlord could share favorable reports with both prospective and current tenants, or a hotel could share environmental quality reports with guests. As another example, government sites could provide feedback to regulators and environmental quality compliance monitors. Regulated industries, such as food production, pharmaceutical production, healthcare facilities (hospitals and clinics), oil drilling sites, mines, power plants and utility companies, chemical production plants, paper mills, steel mills, and other regulated industries could be monitored for environmental quality compliance and/or safety compliance by a governmental compliance officer, or an insurance company officer. Compliance data can be transmitted to a government or insurance company compliance server, perhaps for later use. An individual or an organization can receive discounts and/or tax credits for maintaining compliance, as well as special certifications from the government, an insurance company or other overseeing compliance group. Such information also enables insurance companies and regulators to set environmental quality levels using data driven techniques, instead of relying on arbitrary opinions of scientists and environmentalists.

Figure 6:
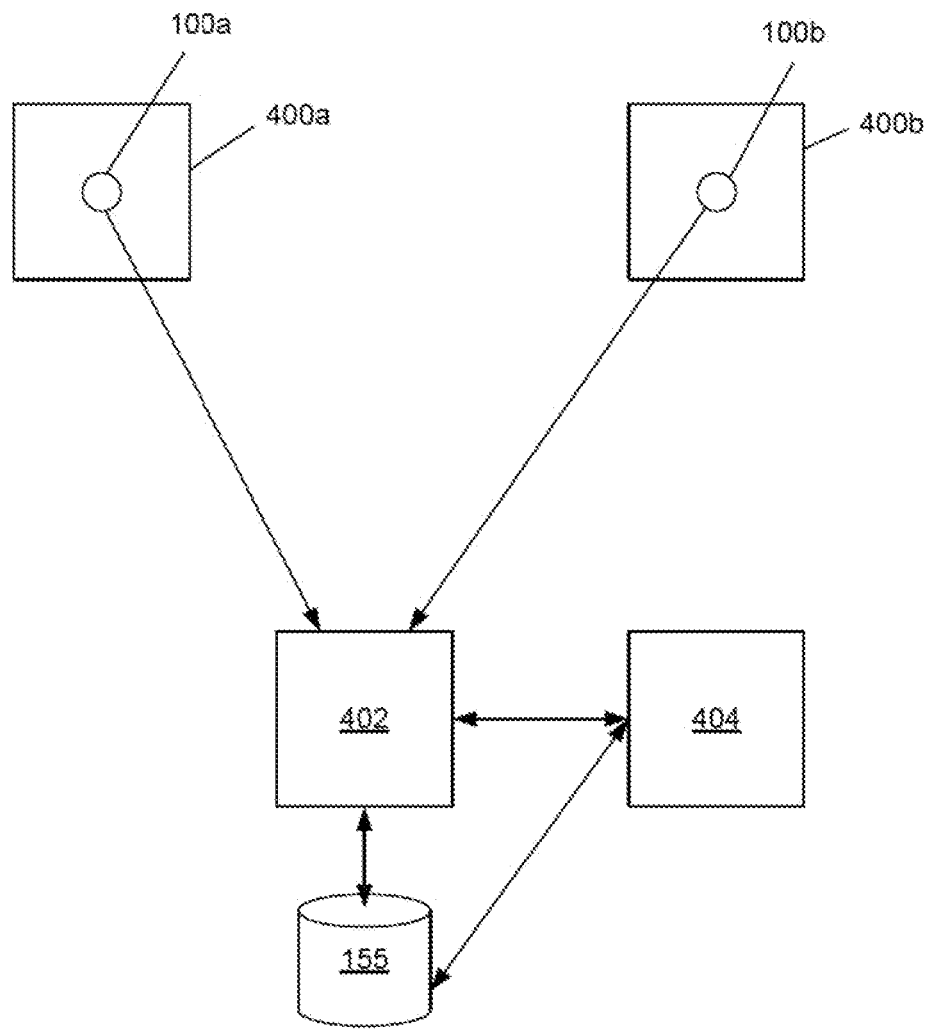
FIG. 6 is a variation of a network diagram for monitoring the environmental quality at multiple environmental locations.

FIG. 6 illustrates that a first sensor system 100a can be located in a first environment 400a. A second sensor 100b can be located in a second environment 400b. The first and second sensor systems 100 can transmit their respective environmental data across a network to one or more servers 402 (referred to non-limitingly as singular or plural herein, there can be a single server or a bank of local or distributed servers). The servers 402 can store the data in a first database in memory 155 that can be in or networked to the servers 402. The servers 402 can be in network communication with second computers 404.

The first and second sensor systems 100a and 100b can detect environmental data relating to environmental quality factors from the first and second environments 400a and 400b, respectively, and at first and second times. The first and second sensor systems 100a and 100b can be in network communication with the server 402 and send the server 402 the environmental data from the first and second environments 400a and 400b (i.e., first and second sensor system data, respectively). The server 402 can process the received environmental data, and save or otherwise store the environmental data and the processed environmental data from the first and second environments 400a and 400b into the data storage device or system 155.

The sensor systems 100, server 402, and/or data storage system 155 can encrypt the data, certify the data (e.g., attach a key to verify that the data originated from the environments 400a and 400b), time-stamp the data when the data was received, attach location data (e.g., from a GPS device in or in communication with the sensor systems 100, server 402, and/or data storage system 155, or combinations thereof), or combinations thereof.

The second computer 404 can request the direct environmental data from the first and second environments 400a and 400b or data derived or processed therefrom, from the server 402 which can retrieve the requested data from the data storage system or device 155 and send the data to the second computer 404. The second computer 404 can request the data directly from the data storage system 155 without requesting the data from the server 402.

For example, the server 402 can process the environmental data from the sensor systems 100a and 100b and store the processed data in the data storage system 155. The server 402 or second computer 404 can compare the first environment data at a first time to the second environment data at a first time and/or to first environment data at a second time. The data comparison can be used to calculate the change from the first time to the second time and/or between the first and second environments.

The server 402 can alter or assign in the first database the value, such as a monetary value, of real and/or personal property listed for the environments 400a and 400b. The personal property and the respective values listed in the first database can be partially or completely linked over a network to a second database (on the first data storage system 155 or a second data storage system), such as an inventory tracking database on a second server. The linked data between the first and second databases can be updated instantly when a change is made to either database, can be updated with a delay, can be updated with manual approval of the respective change, or combinations thereof. The second database (and therefore the first database) can have property listing and expected market value data updated from a third or fourth database, such as from inventory management and market price tracking databases.

The alteration or assignment of the value by the server 402 can depend at least partially on the comparison of the data of the first environment compared to the data of the second environment and/or the current data of the first environment compared to the data of the first environment at the second time. The server 402 alteration or assignment of the value can depend at least partially on a market value for the property and/or the inventory quantity and age of the property (e.g., for perishable goods, such as produce). The server 402 can retrieve the updated or historical market value for the product from a networked computer or memory (e.g., a networked computer or memory recording commodities trading prices for the product). The server 402 can calculate—and record in the database 155—the changes in economic value and/or environmental quality data for the first and/or second environments compared to each other, over time (e.g., at a first time and a second time), compared between different environmental factors (e.g., comparing the particles of cedar pollen to the particles of grass pollen, or the time change of each), or combinations thereof. The sensor array can be attached to the environment of the products (e.g., to an inside wall of a shipping container) and/or to the product or the product's packaging.

The second computer 404 can access the alteration (i.e., the change in value) or assignment (i.e., the entire value) of the first and/or second property values stored in data storage system 155.

Part or all of the system 100 can be stationary. A component of the system 100 can ping any Bluetooth low energy device near the component of the system 100 to retrieve GPS values so that the component or system 100 can verify its location. The system 100 can transmit its location, for example in when the emergency alarm is activated.

The examples and illustrations included herein show, by way of illustration and not of limitation, specific variations in which the subject matter may be practiced. Other variations may be utilized and derived therefrom, such that structural elements and method process substitutions, combinations, and changes may be made without departing from the scope of this disclosure. As a person skilled in the art will recognize from the previous detailed description and from the figures and claims, modifications, combinations, and changes can be made to the disclosure without departing from the scope of this disclosure.

We claim:

1. An environmental monitoring method comprising:
    sensing with an environmental quality monitoring system an environmental quality in a first environment, the sensing comprising producing environmental data;
    encrypting the environmental data in the environmental quality monitoring system before the environmental data is remotely stored;
    attaching a certification to the environmental data to certify that the environmental data originated from the environmental quality monitoring system;
    storing the encrypted environmental data with the attached certification in a remote data storage device, wherein the encrypted environmental data is not accessible by an administrator managing the data storage device;
    transmitting the encrypted environmental data with the attached certification from the remote data storage device to a first computer; and
    decrypting the environmental data and generating a report from the environmental data on the first computer, wherein the certification that verifies data origin is attached to the report.

2. The method of claim 1, wherein the environmental data comprises environmental quality data and location data.

3. The method of claim 2, further comprising pinging with the environmental quality monitoring system a Bluetooth device within range of the environmental quality monitoring system, wherein the pinging comprises the environmental quality monitoring system retrieving at least a part of the location data.

4. The method of claim 1, wherein the environmental data comprises environmental quality data and a collection time for the environmental quality data.

5. The method of claim 4, wherein the environmental data further comprises location data.

6. The method of claim 1, wherein the encrypting comprises encrypting with an encryption key, and wherein the encryption key is accessible in a password-encoded first account on a server.

7. The method of claim 6, further comprising authorizing access for a second account, wherein the authorizing comprises the first account sending the encryption key to the second account.

8. The method of claim 7, wherein the sending comprises the server attaching a certification data to the at least one of the decrypted environmental data or the encryption key to the second account.

9. The method of claim 6, further comprising authorizing access for a second account, wherein the authorizing comprises sending the decrypted environmental data to the second account.

10. The method of claim 6, further comprising attaching by the server a timestamp to the environmental data.

11. The method of claim 1, further comprising attaching a decryption key to an environmental sensor, wherein the sensing of the environmental quality data comprises sensing with the environmental sensor.

12. An environmental monitoring method comprising:
    sensing environmental quality data in a first environment with an environmental quality monitoring system;
    establishing a connection between the environmental quality monitoring system and a Bluetooth device within range of the environmental quality monitoring system, wherein the environmental quality monitoring system retrieves location data from the Bluetooth device via the connection;

attaching the location data to the environmental quality data to form composite data;

recording the composite data in a first database; and transmitting the composite data from the first database to a computer.

13. The method of claim 12, further comprising encrypting the location data before the recording.

14. The method of claim 12, wherein at least a portion of the location data comprises GPS data.

15. The method of claim 12, wherein the transmitting further comprises decrypting the location data.

16. The method of claim 12, wherein the encrypting comprises encrypting with an encryption key, and wherein the encryption key is accessible in a password-encoded first account on a server.

17. The method of claim 16, further comprising authorizing access for a second account, wherein the authorizing comprises the first account sending the encryption key to the second account.

18. The method of claim 17, wherein the sending comprises the server attaching a certification data to the at least one of the decrypted environmental data or the encryption key to the second account.

19. The method of claim 16, further comprising authorizing access for a second account, wherein the authorizing comprises sending the decrypted environmental data to the second account.

20. The method of claim 12, further comprising attaching by the server a timestamp.

21. The method of claim 12, further comprising attaching a decryption key to an environmental sensor, wherein the sensing of the environmental quality data comprises sensing with the environmental sensor.

* * * * *